United States Patent [19]

Gross et al.

[11] 4,302,619

[45] Nov. 24, 1981

[54] CONTROL OF CO EMISSIONS IN A PROCESS FOR PRODUCING GASOLINE FROM METHANOL

[75] Inventors: Benjamin Gross, Cherry Hill, N.J.; Sterling E. Voltz, Media, Pa.

[73] Assignee: Mobil Oil Corporation, New York, N.Y.

[21] Appl. No.: 156,284

[22] Filed: Jun. 4, 1980

[51] Int. Cl.$^3$ ............................ C07C 1/20; B01J 29/28
[52] U.S. Cl. .................................. 585/408; 252/416; 252/417; 252/455 Z; 252/465; 252/470; 585/733
[58] Field of Search ............... 252/416, 417, 418, 419; 585/408, 733

[56] References Cited

U.S. PATENT DOCUMENTS

| | | | |
|---|---|---|---|
| 2,436,927 | 3/1948 | Kassel | 252/417 |
| 3,894,934 | 7/1975 | Owen et al. | 252/417 |
| 4,090,949 | 5/1978 | Owen et al. | 585/408 |
| 4,118,431 | 10/1978 | Chen | 585/733 |

FOREIGN PATENT DOCUMENTS 2438252  2/1975  Fed. Rep. of Germany ...... 585/408

*Primary Examiner*—P. E. Konopka
*Attorney, Agent, or Firm*—Charles A. Huggett; Michael G. Gilman; Charles J. Speciale

[57] ABSTRACT

A process is disclosed for enhancing the conversion of carbon monoxide within the regenerator of a methanol conversion unit used to regenerate spent catalysts from the conversion of methanol by the addition of controlled amounts of either copper chromite, cobalt chromite, or mixtures thereof. Conversion of carbon monoxide in the regenerator is accomplished while maintaining the efficiency of the methanol conversion unit at high levels.

15 Claims, No Drawings

CONTROL OF CO EMISSIONS IN A PROCESS FOR PRODUCING GASOLINE FROM METHANOL

CROSS REFERENCE TO RELATED CASES

United States Patent Application Ser. No. 152,458 filed May 22, 1980 is directed towards solving a similar problem using a platinum metal catalyst. United States Patent Application Ser. No. 047,503, filed June 11, 1979 discloses the use of the same catalyst system to control CO emissions in the catalytic cracking of gas oil to produce gasoline.

BACKGROUND OF THE INVENTION

This invention relates generally to the conversion of methanol so as to produce gasoline and, more particularly, to the control of carbon monoxide emissions resulting from the regeneration of the spent methanol conversion catalyst.

The conversion of methanol to gasoline is an important area of technology which has the potential of becoming even more important as the supply of crude oil is diminished and/or increased in price. Particularly advantageous catalysts which are utilized for the conversion of methanol to gasoline are a special class of crystalline aluminosilicate zeolites of which ZSM-5 is the most preferred member. There are many patents which describe the conversion of methanol to gasoline over said special zeolites, including U.S. Pat. Nos. 3,931,349; 3,969,426; 3,899,544; 3,894,107; 3,907,914; and 3,894,102.

As is known in the art, the catalytic conversion of methanol to produce gasoline over zeolites such as ZSM-5 results in the deposition of carbonaceous material, generally referred to as coke, on the catalyt thereby resulting in decline of activity of said catalyst which must be compensated for by regeneration of the same by burning off said coke at elevated temperatures in the regenerator. The art is well aware that among the products resulting from the combustion of coke are carbon monoxide and carbon dioxide. Recent environmental regulations by the state and Federal governments have seriously limited the amount of carbon monoxide which can be discharged to the atmosphere and, as such, there is need for a process wherein carbon monoxide can be combusted in the regenerator so as to minimize the atmospheric pollution.

Although there is much art involving the combustion of carbon monoxide in a regenerator, this art is really concerned with the catalytic cracking of gas oil to produce gasoline and not the catalytic conversion of methanol to gasoline. Art dealing with the control of carbon monoxide from a catalytic cracking process can be represented by U.S. Pat. Nos. 4,072,600; 4,088,568; and 4,093,535.

In addition, copending application Ser. No. 152,458 filed May 22, 1980 deals with the use of platinum catalysts to control the CO emission in a methanol conversion process to produce gasoline.

SUMMARY OF THE INVENTION

It has now been found that copper chromite, cobalt chromite, or mixtures of the two permit an effective control of carbon monoxide from the effluent gas of the regenerator while still maintaining excellent gasoline yield and quality.

Thus, quite simply put, the instant applicants have discovered that cobalt chromite and copper chromite can function in almost the same manner as platinum-type catalysts, such as those disclosed in copending application Ser. No. 152,458, filed May 22, 1980, since they possess an extraordinarily high activity in connection with CO oxidation activity and yet can be used in such small amounts that they do not have an adverse effect on the gasoline quality and yield. Although copper chromite and cobalt chromite are not as active as the platinum group metals, nevertheless, they do provide an alternative to the use of these metals. Additionally, these catalysts are activities orders of magnitude higher than their individual components. Thus, for example, a copper chromite catalyst has activity with regard to CO oxidation which is orders of magnitude higher than either copper oxide or chromium oxide. It is surprising that these very active catalysts can be used in such minute amounts that they will retain their oxidation activity and yet their hydrogenation/dehydrogenation activity can be suppressed so as not to seriously affect the methanol conversion reaction. The use of copper chromite/cobalt chromite or mixtures thereof provides flexibility with regard to controlling CO emissions to the atmosphere which is mandated by various Federal and state environmental regulations. It is noted that the broad concept of adding copper chromite to the catalyst inventory of a cracking unit is old in the art and is disclosed in U.S. Pat. No. 3,926,778. However, this patent is concerned with the catalytic cracking of gas oil to produce gasoline rather than the conversion of methanol to gasoline. In addition, the amounts of copper chromite which are added in accordance with the teachings of said patent are considerably higher than the level presently contemplated.

DESCRIPTION OF PREFERRED EMBODIMENTS

As has heretofore been stated, the novel process of this invention resides in the addition of copper chromite, cobalt chromite, or a mixture of the two to the catalyst of a methanol conversion unit in amounts such that the conversion of carbon monoxide to carbon dioxide in the regenerator will be considerably enhanced and yet the methanol conversion reaction will be substantially unaffected.

As has heretofore been pointed out, it is known in the art to convert methanol to gasoline utilizing crystalline aluminosilicate zeolites such as ZSM-5. In addition, some of these patents contain teachings that the crystalline aluminosilicate zeolites can have a hydrogenation/dehydrogenation function associated therewith. In this connection, specific mention is made of U.S. Pat. No. 3,969,426, column 3, lines 18–27; as well as U.S. Pat. No. 3,899,544, i.e. see column 3, lines 51–68; as well as claim 8. Quite obviously, if a ZSM-5 type zeolite having a hydrogenation/dehydrogenation component was regenerated in the presence of an appropriate amount of air, said catalyst would inherently oxidize the CO to $CO_2$ even though such is not expressly disclosed in the aforementioned cited patents.

However, the novel process of this invention is not merely concerned with controlling the carbon monoxide emission resulting from the regeneration of spent catalyst, but there is another facet which is critical in the novel process of this invention and that is to accomplish the control of carbon monoxide without substantially affecting the quantity of the gasoline which is produced.

In this connection, although the aforementioned patents involving the conversion of methanol to gasoline with catalysts such as ZSM-5 do, indeed, teach the inclusion of metals having a hydrogenation/dehydrogenation function, nevertheless, there is a difference in the gasoline which is produced depending upon whether or not a hydrogenation component is used and whether or not the conversion is carried out in the presence of added hydrogen. In general, the use of catalysts such as ZSM-5 without an added hydrogenation component and in the absence of added hydrogen results in the production of gasoline in very high yields with small quantities of light gas and practically no production of hydrogen. The gasoline contains large concentrations of paraffins which are mostly isoparaffins and aromatics that has a very high octane level. The gasoline has good stability at reasonable additive levels. However, the gasoline which is produced from the conversion of methanol with ZSM-5 type catalysts having a hydrogenation/dehydrogenation function has a tendency not to be as good as gasoline produced without such restraints due to the fact that there is a potential negative feature involving subsequent dehydrogenation of paraffins to olefins which has a tendency to reduce gasoline stability by increasing gum formation. In addition, dehydrogenation components, in a dehydrogenation environment can increase the dealkylation of toluene to benzene—a completely undesirable aspect, particularly in view of environmental regulations on the benzene content of gasoline. It is noted that in the conversion of methanol with catalysts such as ZSM-5 in the absence of hydrogenation/dehydrogenation components that only trace amounts of benzene are formed. In addition, most of the aromatics are methyl substituted benzenes and, as indicated earlier, it is not desirable to dealkylate these compounds to benzene.

Thus, quite simply put, the novel process of this invention resides in maintaining all the advantages of converting methanol to gasoline with catalysts such as ZSM-5 that are inherent to such a system when it is carried out in the absence of added hydrogen and the absence of dehydrogenation/hydrogenation components and yet to still have the benefit with regard to CO oxidation activity that inherently results from using a hydrogenation component with ZSM-5. This is accomplished by carefully controlling the amount of copper chromite, cobalt chromite, or mixtures thereof which are added to the ZSM-5 type zeolite such that substantially no hydrogenation/dehydrogenation activity is present in the reactor because of the low level of metals which are used, yet these metals will still provide sufficient oxidation activity in the regenerator to catalyze the combustion of CO to $CO_2$. This is accomplished by seriously limiting the amount of copper chromite, cobalt chromite or mixtures thereof to a level not to exceed 500 ppm and more preferably about 50–150 ppm based on total catalyst inventory. It has been discovered that unless the copper chromite and/or cobalt chromite concentration in the catalyst inventory of a conversion unit is limited to no more than 500 ppm that unacceptable gasoline make will occur. It is noted that concentrations of from 1–50 ppm are also desirable, particularly at high regenerator temperatures. It is, indeed, surprising that catalysts containing these low levels of copper chromite and/or cobalt chromite would possess sufficient oxidation activity in the regenerator to effectively control carbon monoxide emission and yet have their dehydrogenation/hydrogenation activity sufficiently minimized so as to not detrimentally affect the methanol conversion reaction.

Two major variants for converting methanol are fluid processes and fixed bed processes. In both of these processes the methanol feed and the catalyst are contacted and then disengaged; the catalyst is regenerated with concurrent and/or countercurrent air; and the regenerated reflexively heated catalyst recontacted with more feed to repeat the operation. These two proceses differ substantially in the size of the catalyst particles utilized in each and also in the engineering of materials contact and transfer which is at least partially a function of the catalyst size.

In fluid processes, the catalyst is a fine powder of about 10 to 200 microns, preferably about 780 micron, size. This fine powder is generally propelled upwardly through a riser reaction zone suspended in and thoroughly mixed with methanol feed. The coked catalyst particles are separated from the conversion products, and after purging are transferred into the regenerator where coke is burned to reactivate the catalyst. Regenerated catalyst generally flows downward from the regenerator to the base of the riser.

In one typical example of a fixed bed process the catalyst is in the shape of beads or pellets having an average particle size of about one-sixty-fourth to one-fourth inch, preferably about one-eighth inch. Active, hot catalyst particles are contacted with a charge stock in a fixed bed reaction zone. In this zone feed is converted while coke is deposited on the catalyst. At the lower end of the reaction zone the products are separated from the coked catalyst and recovered. The coked catalyst is then regenerated in air. Two flue gases comprising carbon oxides are produced. Regenerated catalyst, after removal of coke therefrom, may be reused.

It is to be understood that the particular method of adding copper chromite, cobalt chromite, or mixtures thereof to the catalyst is not critical and, in fact, it can be performed in a number of different ways. The copper and cobalt chromite may be a component of all of the catalyst particles or only of some of the catalyst particles. In terms of its concentrations in the entire system, it must be present in a large enough proportion to be able to effect the reaction of carbon monoxide with oxygen to carbon dioxide provided the conditions during catalyst regeneration are otherwise sufficient to support this combustion, i.e. sufficiently high temperature and sufficient air. Yet is must not be present in a proportion so large that it substantially adversely affects the operation of the conversion side of the process. In this regard, it is important to note that in some instances it may be desirable to cause substantially all of the carbon burned during regeneration to be oxidized all the way to carbon monoxide. Because of the inherent advantages stemming from the use of the novel process of this invention, the refiner is able to increase the regenerator temperature by burning some of the carbon monoxide therein, burning the rest outside the regenerator; for example, in a steam generating CO boiler. Quite obviously, the preferred embodiments of this invention reside in burning all of the carbon monoxide within the regenerator since this obviates the need of a CO boiler which may be necessary in order to meet the various governmental environmental regulations concerning CO emission to the atmosphere.

A convenient method of adding copper or cobalt chromite to the catalyst is to form a mixture of copper or chromium chromite with an inorganic oxide such as alumina and to add the alumina containing the copper or cobalt chromite or mixtures thereof either to the conversion catalyst per se or any component thereof prior to introduction of the same into the conversion unit. Another method of adding the oxidation catalyst to the conversion unit would be to introduce the alumina-containing cobalt or chromium oxide directly into a unit which already contains conversion catalysts, said introduction being accomplished either by adding it to the regenerator or to the unit. It is to be understood, however, other inorganic oxides besides alumina can be used. Other suitable materials include silica-alumina, silica-magnesia, clays, etc.

The expression copper chromite as used throughout the specification and the claims is intended to define a well known class of compounds whose formula is usually designated $XCuO \cdot Cr_2O_3$, wherein X is a value of from 0.5 to 2.5. This material is well known in the art and is disclosed in various United States patents, such as U.S. Pat. Nos. 3,767,595; 3,374,184; and 3,899,446; including the articles and patents mentioned therein.

The methanol conversion catalyst used in the method described herein comprises a crystalline aluminosilicate zeolite which is a member of a novel class of zeolites exhibiting some unusual properties. These zeolites induce profound transformation of aliphatic hydrocarbons to aromatic hydrocarbons in commecially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egrees from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-secion than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing, continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at a 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "contraint index" is calculated as follows:

$$\text{Constraint Index} = \frac{\log_{10}(\text{fraction of n-hexane remaining})}{\log_{10}(\text{fraction of 3-methylpentain remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |

| CAS | C.I. |
|---|---|
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which is incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cation in the forming solution may not be absolutely essential to the formation of this type zeolite; however, the presence of these cations does appear to favor the formation of this special type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina ratio of at least about 12 and a dried crystal density of not less than about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 100 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that unusual sustained activity and stability of this class of zeolites is associated with its high crystal anionic framework density of not less than about 1.6 grams per cubic centimeter. This high density, of course, must be associated with a relative small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite is generally within the approximate range of 0.01 to 40 microns.

The zeolites used in the instant invention can have the original cations associated therewith replaced by a wide variety of other cations according to techniques well known in the art. Typical replacing cations would include hydrogen, ammonium and metal cations including mixtures of the same. Of the replacing metallic cations, particular preference is given to cations of metals such as rare earth metals, manganese and calcium.

Typical ion exchange techniques would be to contact the particular zeolite with a salt of the desired replacing cation or cations. Although a wide variety of salts can be employed, particular preference is given to chlorides, nitrates and sulfates.

Representative ion exchange techniques are disclosed in a wide variety of patents, including U.S. Pat. Nos. 3,140,249; 3,140,251; and 3,140,253.

Following contact with the salt solution of the desired replacing cation, the zeolites are then preferably washed with water and dried at a temperature ranging from 150° F. to about 600° F. and thereafter calcined in air or an inert gas at temperatures ranging from about 500° F. to 1500° F. for periods of time ranging from 1 to 48 hours or more.

Prior to use, the zeolites should be dehydrated at least partially. This can be done by heating to a temperature in the range of 200° to 600° C. in an atmosphere, such as air, nitrogen, etc. and at atmospheric or subatmospheric pressures for between 1 and 48 hours. Dehydration can also be performed at lower temperatures merely by using a vacuum, but a longer time is required to obtain a sufficient amount of dehydration.

Operating conditions generally include temperatures between about 500° F. and about 850° F. and pressures between 0 and 500 psig. For fluid bed operation, the temperature is preferably between about 600° and about 850° F. and the pressure between about 0 and about 200 psig. For fixed bed operation, the temperature is preferably between about 600° F. and about 750° F. and the pressure between about 100 and about 500 psig. The liquid hourly space velocity is generally between 0.1 and 10, preferably between 0.5 and 4.

The zeolites utilized in this invention are preferably incorporated or otherwise admixed with a matrix. Matrix materials are well known in the art and include inorganic oxides such as clay, silica, alumina, silica-alumina, etc. The matrix which is used is preferably non-catalytic—with alumina being particularly preferred.

What is claimed is:

1. In a process for the catalytic conversion of methanol to produce products boiling in the motor fuel range, wherein said methanol is contacted with a porous acidic solid catalyst comprising a crystalline aluminosilicate zeolite having a pore diameter greater than about 5 Angstroms, a silica-to-alumina ratio of at least 12, and a constraint index within the range of 1–12 at elevated temperatures, in a reaction vessel at conversion conditions including elevated temperatures and the absence of added hydrogen so as to convert said methanol to lower molecular weight products with deposit on said catalyst of a deactivating solid carbonaceous contaminant resulting from said conversion, the so deactivated catalyst being transferred to a regeneration vessel in which oxidation of said carbonaceous deposit proceeds in the presence of air with generation of carbon monoxide and carbon dioxide and the regenerated catalyst at elevated temperature is transferred from said regeneration vessel to said reaction vessel to catalyze further conversion, the improvement which comprises:

conducting said conversion and said regeneration with an inventory of said solid, porous, acidic solid catalyst particles and particles of an oxidation catalyst selected from the group consisting of copper chromite, cobalt chromite, or mixtures thereof and limiting the concentration of said oxidation catalyst to an amount great enough to promote oxidation of CO and inadequate to substantially affect the dealkylation of aromatics in said reaction vessel as compared with a like catalyst free of such metal, said amount being less than 500 ppm based on total catalyst inventory.

2. The process of claim 1 wherein said crystalline aluminosilicate is ZSM-5.

3. The process of claim 1 wherein said crystalline aluminosilicate is ZSM-11.

4. The process of claim 2, wherein said oxidation catalyst is copper chromite.

5. The process of claim 2, wherein said oxidation catalyst is cobalt chromite.

6. The process of claim 4, wherein copper chromite is present in an amount ranging from 50–150 ppm.

7. The process of claim 5 wherein the cobalt chromite is present in an amount ranging from 50–150 ppm.

8. The process of claim 5 wherein the cobalt chromite is present in an amount ranging from 1–50 ppm.

9. The process of claim 4 wherein the copper chromite is present in an amount ranging from 1–50 ppm.

10. The process of claim 3 wherein said oxidation catalyst is copper chromite.

11. The process of claim 3 wherein said oxidation catalyst is cobalt chromite.

12. The process of claim 10 wherein copper chromite is present in an amount ranging from 50–150 ppm.

13. The process of claim 11 wherein the cobalt chromite is present in an amount ranging from 50–150 ppm.

14. The process of claim 11 wherein the cobalt chromite is present in an amount ranging from 1–50 ppm.

15. The process of claim 10 wherein the copper chromite is present in an amount ranging from 1–50 ppm.

* * * * *